United States Patent
Holmbom et al.

[19]

[11] Patent Number: 5,964,984
[45] Date of Patent: Oct. 12, 1999

[54] METHOD AND APPARATUS FOR WORKING UP A SAMPLE OF LIQUID

[76] Inventors: Bjarne Holmbom, Skarpskyttegatan 14, Abo, Finland, Fin-2054D; Johan Roeraade, Sagvagen 4, Tumba, Sweden, S-147 40; Matthew Rice, Forskarbacken 11/604, Stockholm, Sweden, S-104 05

[21] Appl. No.: 08/894,195

[22] PCT Filed: May 28, 1996

[86] PCT No.: PCT/FI96/00301

§ 371 Date: Dec. 22, 1997

§ 102(e) Date: Dec. 22, 1997

[87] PCT Pub. No.: WO96/38719

PCT Pub. Date: Dec. 5, 1996

[30] Foreign Application Priority Data

Jun. 1, 1995 [FI] Finland .................................. 952688

[51] Int. Cl.⁶ ................................ D21C 7/06; D21F 1/08
[52] U.S. Cl. ............................ 162/49; 162/198; 162/263; 210/768; 210/791; 210/85; 210/415; 73/863.23; 73/863.24; 73/863.83
[58] Field of Search ............................. 162/49, 198, 263; 210/739, 745, 767, 768, 791, 85, 92, 93, 106, 107, 413, 414, 415; 73/863.23, 863.24, 863.83

[56] References Cited

U.S. PATENT DOCUMENTS

| | | | |
|---|---|---|---|
| 4,409,853 | 10/1983 | Chase et al. | 162/49 |
| 4,693,815 | 9/1987 | Collins, Jr. | 210/107 |
| 5,104,485 | 4/1992 | Weyer | 162/198 |
| 5,366,592 | 11/1994 | Ford | 162/198 |
| 5,518,584 | 5/1996 | Aikawa | 162/49 |
| 5,542,542 | 8/1996 | Hoffmann et al. | 162/49 |
| 5,643,411 | 7/1997 | Ford | 162/49 |

FOREIGN PATENT DOCUMENTS

| | | |
|---|---|---|
| WO 94/27134 | 11/1994 | European Pat. Off. . |
| 93902 | 2/1995 | Finland . |
| 95319 | 9/1995 | Finland . |
| 95839 | 12/1995 | Finland . |
| 9200175 | 7/1993 | Sweden . |
| 1257964 | 12/1997 | United Kingdom . |

*Primary Examiner*—Robert J. Popovics
*Attorney, Agent, or Firm*—Nixon & Vanderhye P.C.

[57] ABSTRACT

A method and apparatus act on a sample liquid of a pulp and paper industry process water, such as a pulp slurry or white water. The sample is acted upon in an apparatus including sample flow chamber, a filtrate flow chamber, and a filter connecting the sample flow chamber with the filtrate flow chamber. A flow sample liquid, including solid substances such as fibers and filler materials (as well as dissolved and colloidal substances) is introduced through an inlet into the sample flow chamber. A main flow of the sample liquid is discharged through an outlet. A flow of filtrate is passed through a filter from the sample flow chamber into the filter flow chamber, thereby separating a predetermined fraction of solid substance from a minor portion of the introduced flow of sample liquid, in the filter. The minor portion of sample liquid corresponds to less than 1%, typically less than 0.1%, of the total introduced flow of sample liquid. A mat of solid substances is prevented from building up on the inlet side of the filter by inducing in the sample flow chamber turbulence or a high flow velocity of sample liquid adjacent the filter.

23 Claims, 6 Drawing Sheets

METHOD AND APPARATUS FOR WORKING UP A SAMPLE OF LIQUID

BACKGROUND AND SUMMARY OF THE INVENTION

The present invention refers to a method and apparatus for working-up a sample liquid of a pulp and paper industry process water, such as pulp slurry or white water, in an apparatus including a sample flow chamber, a filtrate flow chamber and a filter connecting said sample flow chamber with said filtrate flow chamber.

Due to environmental concerns and the rising cost of chemical additives, paper mills are tending to increasingly close the wet end of the paper machine. This leads to accumulation of dissolved and colloidal substances (DCS), originating from the wood fibers and, as a consequence, process disorders. Deteriorated runability and/or inferior paper quality are frequently experienced. Various chemicals are added to reduce these problems, but the physio-chemical and chemical interactions between DCS and such compounds are complex and often poorly understood. As a result, an overdosage and/or poor utilization of additives is a well known scenario experienced in paper mills.

Considerable laboratory work has been carried out to characterize the chemical nature and behavior of DCS. Such work has provided new and valuable insight into some of the interactions between these components. In order to gain a better knowledge of the dynamics of the chemical interactions, a continuous monitoring of DCS would be of great advantage.

In order to characterize a sample, extraneous material that may hinder or even prevent monitoring and/or analysis equipment from functioning, should be removed. In order to analyze DCS components in e.g. a paper machines white water, varying amounts of fibers and fines present, should be removed.

These fibers (>20 $\mu$m) could theoretically be removed from the DCS (<10 $\mu$m) by size exclusion. Traditional techniques of filtration, however, show the tendency to remove colloidal substances, as well as, fibers, due to an absorption of lipophilic droplets and colloidal particles in the fiber mat formed on the filter. Successful laboratory methods utilize a centrifuge. A method of continuous centrifugation has been proposed, however this requires a large, expensive and inconvenient decanting centrifuge.

It is an object of the present invention to provide a method and an apparatus, for working-up sample liquid, in which above problems have been minimized.

It is a further object of a preferred embodiment of the present invention to provide a method and apparatus of the above type which allows a continuous monitoring of DCS i process water.

It is a still further object of the preferred embodiment of the present invention to provide a method and an apparatus for continuous on-line fractionation of solid and colloidal substances in process water.

Toward the fulfillment of the above mentioned and other objects, the method and the apparatus according to the present invention are characterized by what is stated in the appended claims.

A working-up of a sample liquid of a pulp and paper industry process water can thereby be achieved according to the present invention by introducing a flow of sample liquid, including solid substances, such as fibers and filler materials, and dissolved and colloidal substances, through an inlet into a sample flow chamber, discharging a main flow of such introduced sample liquid through an outlet from the sample flow chamber, leading from the sample flow chamber through a filter a flow of filtrate into an adjacent filtrate chamber, thereby separating in the filter from a minor portion of said introduced flow of sample liquid, corresponding to <1%, typically <0.1% of the total introduced flow of sample liquid, a predetermined fraction of solid substances, and preventing a mat of solid substances from building up on the inlet side of the filter by inducing in the sample flow chamber turbulence or a high flow velocity of sample liquid adjacent the filter.

According to a preferred embodiment of the present invention a flow of filtrate, corresponding to less than or about 0.1% of the total flow of sample liquid introduced into the sample flow chamber, is forced to flow through the filter. Thereby only a small amount of solid substance is separated in the filter and added into the remaining main flow of sample liquid being discharged from the sample flow chamber. The added amount of solid substance is that small that it does not noticeably influence the consistency of the main flow of sample liquid.

The sample flow chamber is according to a most preferred embodiment of the invention a sample flow tank, having a filter inserted flush with the bottom thereof and connected to a filtrate or receiver chamber arranged beneath the bottom.

A mixing device, such as an impeller with rotor blades or other similar elements, is arranged in the sample flow tank, for inducing turbulence and preventing build up of solid substances on the filter. Rotor blades are arranged to move relatively close to the filter, e.g. at a distance h=10–25 mm from the filter. One or several baffles may be placed close to the inner side wall of the vertical sample flow tank to increase turbulence.

The sample flow tank can be a relatively high vertical tank, but can also have the form of an oblong trough, as long as a high velocity flow of sample liquid or turbulence is induced therein to prevent build up of solid material on the filter.

A microporous polymer membrane filter, such as a Whatman Cyclopore™ Track Etched Membrane made of polycarbonate or polyester or similar other brand polymer membrane, may be inserted in the bottom of the sample flow tank. Such filters usually are very smooth and usually have a thickness of about 7–23 $\mu$m, a porosity of about 4–20% and round holes with a pore size of 0.1–12 $\mu$m. Of course other filters, such as woven filters and filters with larger pore sizes e.g. up to 70 $\mu$m can be utilized.

The flow of sample liquid is forced to flow through the sample flow chamber by a circulating pump arranged upstream or a suction pump downstream of the sample flow chamber in the flow of sample liquid. Thereby a high velocity continuous flow of sample liquid is preferably arranged to flow through the sample flow chamber in order to continuously introduce a representative minor flow of sample liquid through the filter.

A valve or a suction pump is arranged in the flow of filtrate downstream of the filter, for controlling the filtrate flow through the filter. The velocity of the filtrate through the filter should be much less than 10 mm/s, typically about 1 mm/s or even less.

The sample flow chamber is according to another embodiment of the present invention a cylindrical through flow housing, having an inlet in one end and an outlet in its other end and further having at least a segment of its cylindrical wall made of filtration medium. The flow of sample liquid is forced to flow at a high velocity along the filtration medium, for preventing build up of solid substances on the inlet side, i.e. the sample flow chamber side, of the filter.

The present invention provides a new sample work-up method and apparatus for continuous on-line fractionation of pulp and paper process waters. Pulp fibers and large fines are selectively removed from the required analytical sample by utilizing a filtration medium as a size exclusion barrier. A high flow rate of process water is passed across one side of the filter medium with only a relatively small volume of sample passing through the filtration medium. Thus a filter cake and subsequent clogging of the membrane can be prevented as the process water consistency is not significantly reduced by the filtration, due to the small filtrate flow and a fast process water turnover and as fibers are continuously stripped from the filter surface due to turbulence, shear and eddy effects, induced by mechanical turbulence inducing means and/or high flow rates.

In the traditional sense, filtration is the separation of a fluid solids mixture involving the passage of most of the fluid through a porous barrier which retains most of the solid particulate contained in the mixture. Usually the filtrate is transferred through the filter either by pressure applied upstream to the filter medium or by vacuum applied to the filtrate.

The new filtration technique is, however, based on the premises that only the quality of filtrate is critical and that the yield of filtrate is of minor importance. We have found, when working-up samples of pulp slurry, that it is possible to eliminate the buildup of a fiber mat (and subsequent absorption of lipophilic droplets) by increasing the turbulence or the flowrate of pulp slurry adjacent the filter and by substantially decreasing the flow of filtrate compared to traditional filtration.

Following mechanisms are believed to have an positive impact on the new filtration technique, when working-up a good analytical sample from process water, such as pulp slurry:

a) Flow of filtrate through filter:
We have found that the flow velocity of filtrate through the filter medium has a great impact on the flow conditions through the filter medium. Too high flow velocity tends to build up a filter cake in the filter. The flow velocity through e.g. a filter with 10 $\mu$m pores, such as Whatman Cyclopore™ membrane, should not exceed 10 mm/s, but should typically be about 1 mm/s, preferably even less 10–15 mm/min. High pressure difference easily causes cake formation on filter surface. The pressure difference over the filter should be less than 0.1 bar, preferably negligible. An agitator, such as a magnetic agitator, may be provided on the outlet side of the filter, if a cake of fines or similar substances tends to build up on the outlet side. Also the filtrate flowrate should be as small as possible, e.g. 10–60 ml/min, depending on the effective filter area, may be enough, in order not to cause hold up and integration of filtrate, where momentary variations in filtrate conditions are diluted in large filtrate volumes.

b) Consistency of sample liquid (process water):
We have found that the factor of process water, e.g. pulp slurry, consistency is important since the quantity of solids present in the water close to the filter has an impact on whether a cake will be formed or not. Local variations in process water consistency over the filter surface may occur resulting in regions of elevated solids content. However, if the process water is uniformly mixed and the quantity of filtrate extracted has negligible influence upon the process water consistency, then such effects are also negligible. Therefore high process water turnover is suggested.

c) Flow profile of sample liquid (process water):
Turbulence, eddy currents and shear forces are invoked in order to strip fibers and solids away from the filter surface. It is essential to have such a sample liquid flow profile that material is continuously being removed from the filter surface by forces within the fluid itself. The shear forces and eddy forces acting close to the filter surface are essential for preventing fibers from either clogging or passing longitudinally through the pores of the filter. The fibers that brush past the filter surface assist additionally by "wiping" the filter surface of fines and other debris that might collect.

A high flowrate of pulp slurry through the sample liquid chamber also provides a continuous relevant sample of liquid in front of the filter.

d) Effect of the filter itself:
Adjacent the filter surface, on the inlet side of the filter, two different forces tend to pull fibers in different directions. Shear forces tend to strip fibers from the filter surface, whereas flow of filtrate tends to pull fibers into the pores of the filter. The filter should therefore preferably be very smooth to prevent fibers from getting caught by the filter surface and be very thin (e.g. <23 $\mu$m, preferably even less) to prevent fibers from being permanently stuck in the filter pores/capillaries. If needed (e.g. for ultra thin filters having a large filter area) the filter can be supported from the filtrate side.

Low flowrates across filters utilized in the system according to the present invention and accordingly low almost negligible pressure drops over these filters allow very thin filters to be used. Already relatively low pressure drops could mechanically damage ultra thin filters, e.g. of a few micrometer thickness.

Depending on pore size certain fractions of fibers, such as fines, and colloidal substances flow easily through thin filters. Larger fibers may momentarily get trapped with their one end in the pores, the other end still protruding out of the filter surface (the filter being very thin). Such protruding fibers are easily stripped off the filter surface by turbulent flow conditions on the inlet side of the filter. Preferably the distance between adjacent pores in a thin filter is (if practically possible) large enough not to allow one fiber from being simultaneously stuck at its both ends in adjacent pores. A thin filter, if momentarily clogged may easily be regenerated by introducing a high velocity flow or highly turbulent flow of pulp slurry over the filter surface, while the flow of filtrate is temporarily halted.

The filter pore size may be selected according to need. A filter having a pore size of about 0.5 $\mu$m may be used to separate fines and colloidal substances, whereas a filter having a pore size of about 70 $\mu$m may be used if a filtrate including larger fines is needed.

BRIEF DESCRIPTION OF THE DRAWINGS

Other features and advantages of this invention will become apparent in the following detailed description of the preferred embodiments with reference to the accompanying drawings, in which.

DETAILED DESCRIPTION OF THE DRAWINGS

Figure 1A:
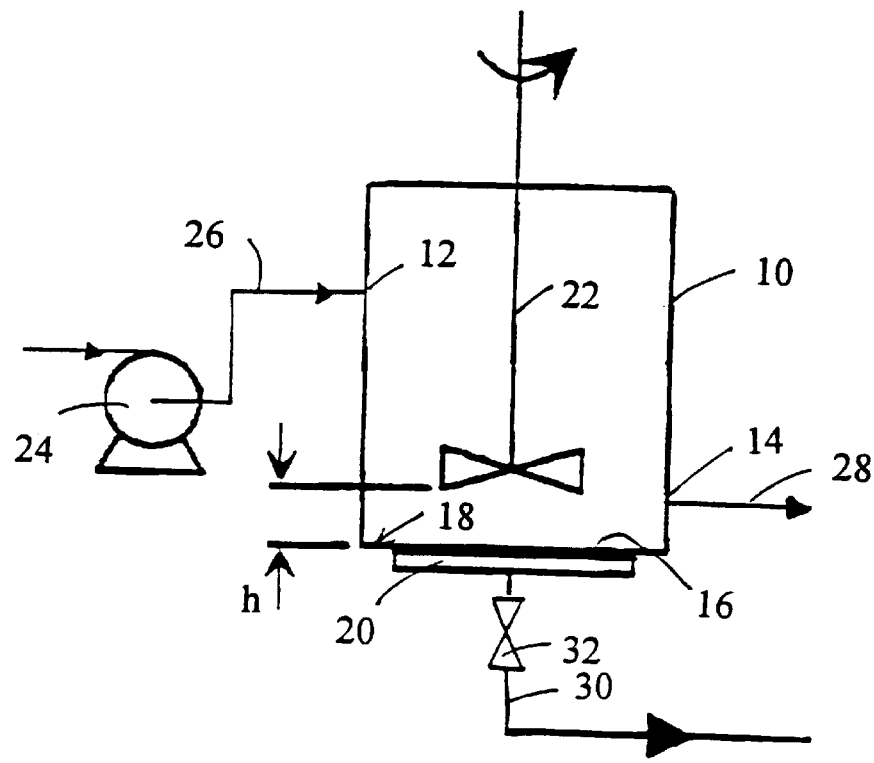
FIGS. 1a and 1b show schematical drawings of apparatuses according to the present invention.

FIG. 1a shows a sample tank 10, having an inlet 12 and an outlet 14 for sample liquid. A plane microporous filter 16 is inserted flush with the bottom 18 of the sample tank, for providing a flow connection with a filtrate chamber 20 beneath the sample tank.

An impeller 22 is positioned in the sample tank 10 at a short distance (h) from the filter, for providing turbulence in the sample tank.

A flow of sample liquid, such as pulp slurry or white water, is pumped with pressurizing pump 24, upstream of the sample tank, through line 26 and inlet 12 into the sample tank and out of the tank through outlet 14 and line 28. Filtrate is discharged from the filtrate chamber 20 through line 30. This filter system operates by over pressure and valve 32 in line 30 controls the flow of filtrate.

Figure 1B:
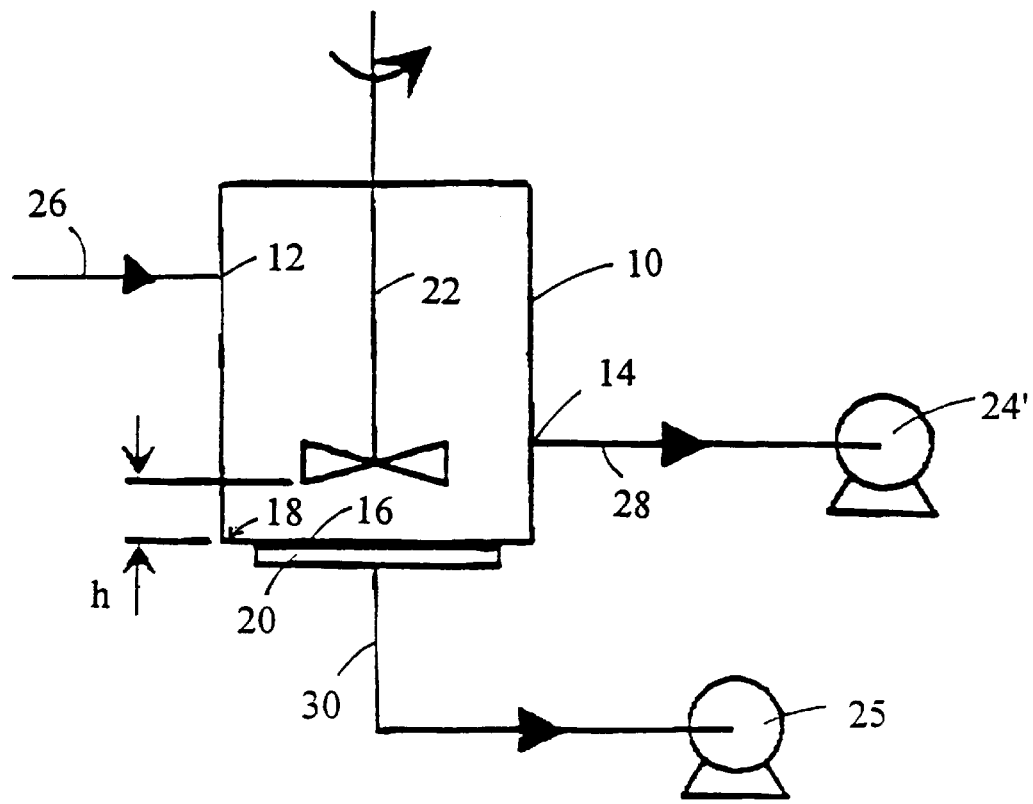

FIG. 1b shows another primary scheme of operation of a sample tank connected to a filter chamber. A pump 24' is placed downstream of the sample tank. A vacuum pump 25, such as a peristaltic pump, is placed downstream of the filter to ensure that the filtrate is under approx. the same pressure (vacuum) as the sample flow.

Figure 2:
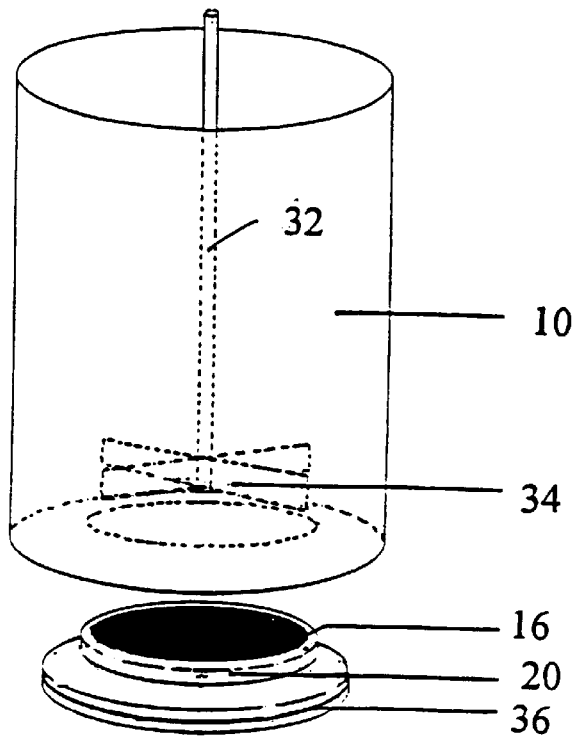
FIG. 2 shows schematically and in more detail a sample tank, the filter and filtrate chamber separated from the sample tank.

FIG. 2 shows in a side view a sample tank 10, having arranged axially in its center an impeller 22, with 4 rotor blades 34 close to the bottom of the tank. The filter 16 and the filtrate chamber 20 and a base plate 36, have been taken apart from the sample tank 10. The filter 16 is a Whatman Cyclopore™ membrane filter. The tank can be made of stainless steel or any other suitable material.

Figure 3:
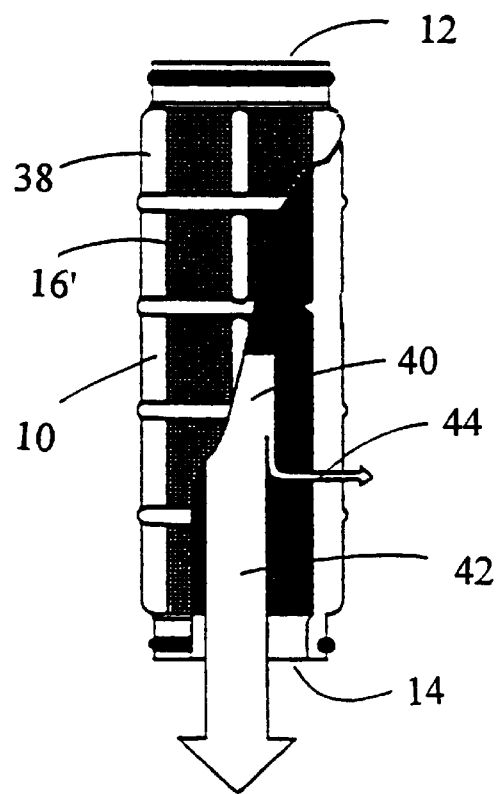
FIG. 3 shows schematically a partly elevational view of another sample chamber according to the present invention.

FIG. 3 shows a cylindrical flow through sample chamber 10, having an inlet 12 at its first end and an outlet 14 at its other end. Cylindrical filter segments 16', e.g. of woven polyester cloth, are inserted in the side walls 38 of the cylindrical chamber. Means not shown are provided to introduce a flow 40 of sample liquid, such as process water, into the sample chamber. A main flow 42 of the sample liquid is discharged through the outlet and a minor flow 44 is directed to flow through the filter.

Figure 4A:
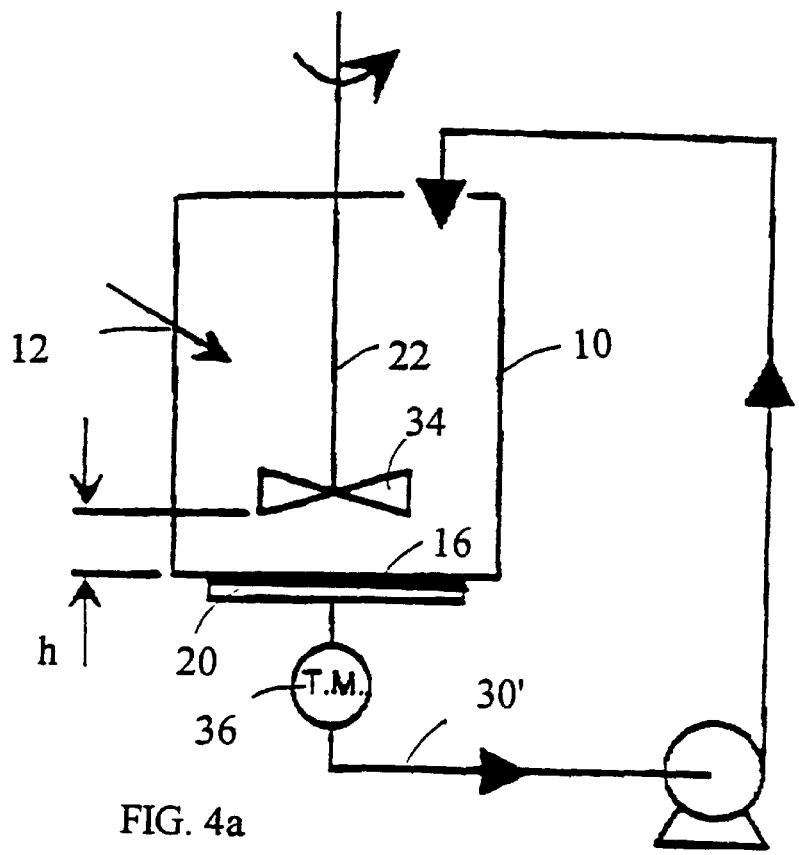
FIGS. 4a and 4b show experimental apparatuses used in experiments 1–4.
Figure 4B:
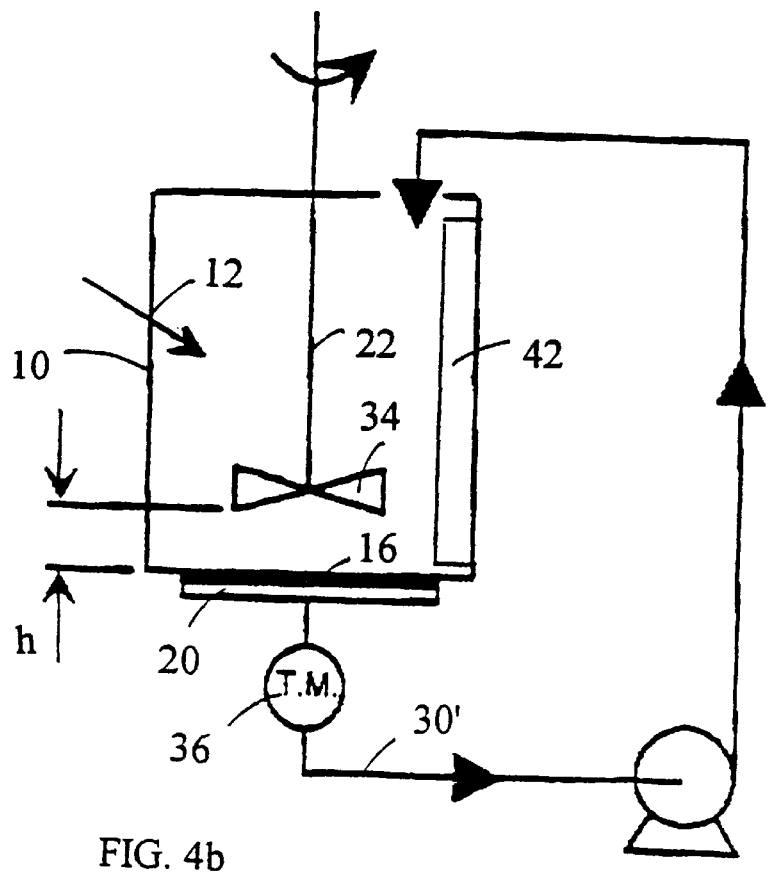

Experiments have been performed in order to study effects of different impeller speeds, filtrate flowrates, additions of filler materials and effect of baffle on filtration conditions of a test apparatus as schematically shown in FIG. 4a and FIG. 4b. A bulk sample of 1,5 wt % TMP (thermomechanical pulp) slurry was introduced through inlet 12 into a sample tank 10 ($\phi$ 280 mm and volume 20 l), having an impeller 22 with rotor blades 34. A filtrate was withdrawn through the filter 16 ($\phi$ 142 mm, thickness 10 $\mu$m, pore size 10 $\mu$m and porosity 8%) and recirculated through line 30' into the tank 10. Turbidity of the filtrate was measured with on-line measuring apparatus 36, to give a value on turbulence, flocculation and sedimentation tendency of fibers and fines in the tank.

EXPERIMENT 1

Effects of different impeller speeds were studied in an apparatus as shown in FIG. 4a. A bulk sample of 1,5 wt % TMP (thermomechanical pulp) slurry without fillers was introduced into the sample tank 10. The rotor blades 34 of the impeller was placed at a distance h=25 mm above the filter membrane 16. A sample flowrate of approx. 10 ml/min was withdrawn from the tank 10 through the filter 16 and circulated back through a line 30' to the bulk slurry in the tank 10.

First the effect of a variation of impeller speed in the range of 200 to 2000 rpm was studied. Thereafter a more detailed study was undertaken with impeller speeds in the range of 1000 to 400 rpm. The impeller speed was altered only when the turbidity reading was deemed stable. No other parameters were varied during this experiment.

Impeller speeds >1000 rpm resulted in considerable vortexes forming within the tank and membrane filter damage. Impeller speeds less than 300 rpm resulted in cake formation on the filter.

Figure 5:
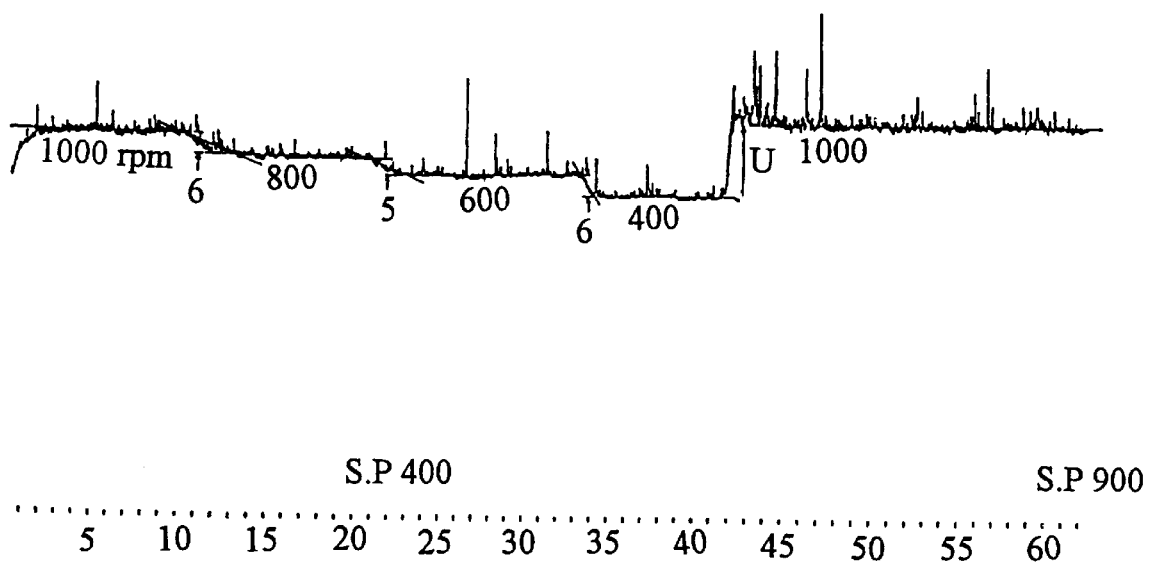
FIGS. 5 to 7 show turbidity charts for experiments 1–4.

The most stable range of operation appeared to exist between 400 and 1000 rpm as no filter damage or cake formation occurred during these experiments. It appears that for the given conditions, impeller speed is linearly proportional to the change in turbidity. A turbidity chart for varying impeller speeds in the range of 1000–400 rpm is shown in FIG. 5.

EXPERIMENT 2

Effects of different filtrate flowrates was studied in an apparatus shown in FIG. 4a. A bulk sample of 1,5 wt % TMP slurry without fillers was introduced into the sample tank 10. The rotor 34 was placed approx. 25 mm centered above the filter membrane 16 and set to 600 rpm.

Figure 6:
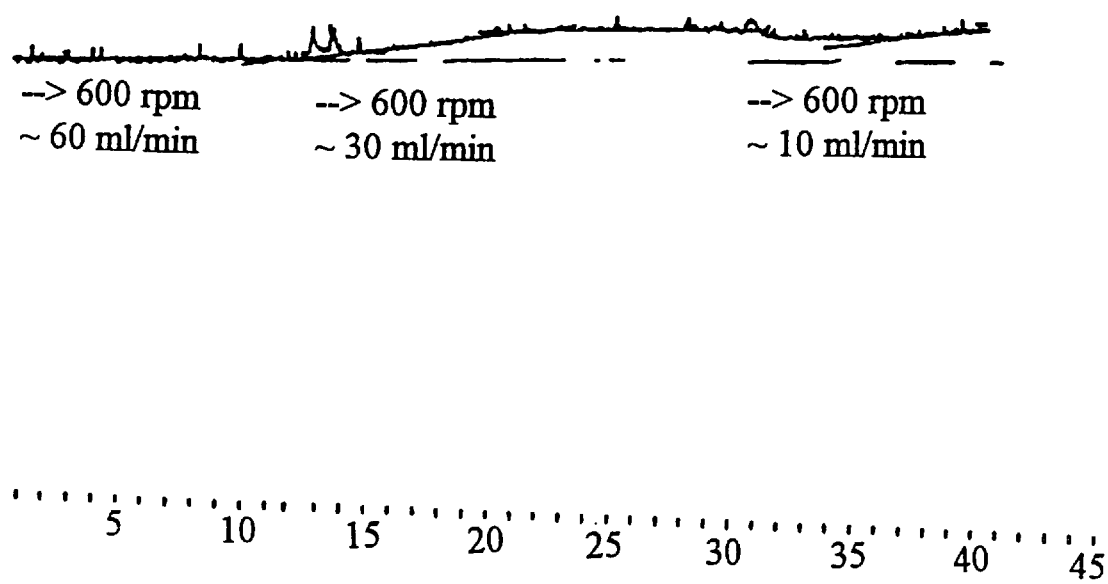

The filtrate flowrate was set to approx. 600 ml/min, 60 ml/min, 30 ml/min or 10 ml/min. After a few minutes of operation at 600 ml/min a thick filter cake formed on the filter 16. The experiment was continued for at the lower flowrates (60–10 ml/min). The obtained turbidity charts are shown in FIG. 6. Extremely low flowrates (10 ml/min) resulted in fines flocculation and sedimentation in the receiver chamber below the membrane filter. A stirrer may be disposed in the receiver chamber to avoid this. 60 ml/min appeared to be a good choice of filtrate flowrate for this experiment.

EXPERIMENT 3

Effects of addition of filler materials in the bulk sample was studied in apparatuses shown in FIG. 4a and 4b. The apparatus shown in FIG. 4b differs from the apparatus in FIG. 4a in that a baffle 42 is placed vertically on the side wall of the sample tank 10 in order to increase turbulence therein.

A bulk sample of 1,5 wt % TMP slurry with 0,5 wt % clay filler material was introduced into the tank 10. The first part of the experiment was performed in an apparatus shown in FIG. 4a with the rotor 34 placed approx. 25 mm centered above the filter membrane 16. In the second part of the experiment the apparatus was modified by including a single wooden baffle 42 into the tank, as shown in FIG. 4b. The baffle was positioned approx. 10 mm from the base of the tank 10. Both filtrate flowrate and impeller speed were varied in the experiments.

Figure 7:
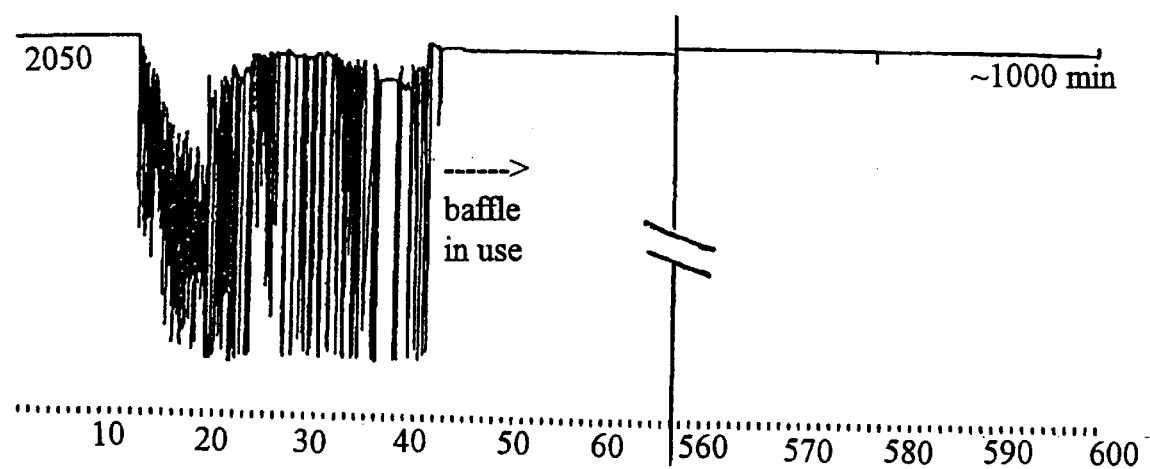

The experiment showed that a TMP slurry including filler material led to a filter blockage after ca. 15 minutes of operation when using an apparatus without a baffle, as shown in first (left) part of turbidity chart in FIG. 7. The addition of a baffle, as shown in FIG. 4a, resulted in the disruption of the vortex formed in the tank and a considerably increased turbulence within the tank.

Flowrates greater than 100 ml/min and impeller speeds less than 200 rpm resulted also in cake formation and subsequent blockage, when using the apparatus shown in FIG. 4b. However, with impeller speeds kept sufficiently high (>500 rpm) and flowrates kept low (<60 ml/min) the apparatus operated, without filter fouling, for extended periods (>1000 min) and a consistent filtrate was obtained, as can be seen from the second (right) part of turbidity chart shown in FIG. 7.

It can be concluded from the experiment that the increased turbulence of the bulk sample by incorporation of a baffle prevented the formation of a filter cake, i.e. turbulence prevented the sedimentation of the heavier filler materials.

The membrane filter material used is extremely resilient to harsh treatment. Even after successive periods (several hours each) of severe cake formation with significant under pressure in the receiving line, the filter could be regenerated. The method of regeneration was straightforward and required no backflush as would be needed with traditional filter matrices.

The procedure was simply to stop the filtrate flow, remove the baffle and to use high impeller speeds (around 1500 rpm) for approx. 1 minute and thus wipe the filter surface clear of debris. Following this, the impeller was set at the original value (600 rpm), the baffle was reinstalled and the filtrate pump was restarted (60 ml/min).

The experiment shows that the turbulence of the bulk sample (above the filter) in the tank is essential to prevent cake formation and subsequent filter blockage. A filtrate flowrate of approx. 60 ml/min gave consistent results. Higher flowrates (>100 ml/min) resulted in cake formation and subsequent filter blockage.

EXPERIMENT 4

Effects of further addition of filler materials and the increase of turbulence by altering the location of the propeller was studied. A bulk sample of 1,5 wt % TMP slurry with 1,0 wt % filler material was introduced into the tank shown in FIG. 4b (filtrate flowrate; 60 ml/min, 600 rpm rotor speed).

After approx. 2 hours of operation a cake gradually formed on the filter leading to complete blockage. The turbulence of the bulk slurry was increased by lowering the rotor 34 of the impeller from about 25 mm to 10 mm above the filter surface. This increased the turbulence of the bulk slurry and restored the system. At a flowrate of 60 ml/min, a stable turbidity measurement was obtained for an extended period of time.

As an over all c conclusion can be noticed that:

A too high flowrate (>100 ml/min) resulted in filter fouling.

Extremely low filtrate flowrates (<10 ml/min) resulted in excessive fines accumulation within the system.

A suggested ideal operating flowrate is 60 ml/min. This is of course dependent upon the size and porosity of the filtration medium. In terms of velocity through the membrane pores, this relates to approx. 1 mm/s for the filter used in these experiments.

High turbulence is required in order to keep the bulk pulp and filler slurry suspended and to prevent cake formation and subsequent filter fouling.

The type of filter material is extremely critical for this experiment to work. The ability of the used filter to avoid damage through pore blockage is a key feature.

In above experiments a special very smooth polycarbonate filter membrane having a thickness of 10 μm and pore size of 10 μm has been used. It is obvious that other types of filters, such as woven filters, can be used in an apparatus according to the present invention. Larger pore sizes, e.g. up to 70 μm, can be used as long as, consistent filtrate is achieved. Larger pore size filters can e.g. be used in connection with retention measurements.

The present invention provides a fast and reliable method and apparatus for separating fibers and fines from a sample flow of pulp slurry before analyzing colloidal and dissolved substances. The invention also provides means for testing the impact of different chemicals on a liquid, such as a pulp slurry. The invention can e.g. be used to measure fines passing the filter when using different retention agents, in order to compare the effect of different agents.

While the invention has been described in connection with what is presently considered to be the most practical and preferred embodiments, it is to be understood that the invention is not to be limited to the enclosed embodiments, but on the contrary, is intended to cover various modifications and equivalent arrangements included within the spirit and scope of the appended claims.

We claim:

1. A method of obtaining a filtered sample for the determination of at least one of dissolved and colloidal substances, using a sample flow chamber, a filtrate flow chamber, and a filter connecting the sample flow chamber with the filtrate flow chamber, comprising:

(a) introducing a flow of sample liquid, including solid substances and at least one of dissolved and colloidal substances, into the sample flow chamber;

(b) discharging a primary flow of sample liquid from the sample flow chamber;

(c) separating a minor flow of sample liquid from the sample flow chamber corresponding to less than 1% of the flow of sample liquid from (a), and passing the minor flow through the filter into the filtrate chamber to produce a solid substance removed from the flow of sample liquid to provide a filtered sample in the filtrate chamber which is suitable for use for the determination of at least one of dissolved and colloidal substances therein; and (d) inducing turbulence or a high flow velocity of sample liquid in the sample flow chamber adjacent the chamber sufficient to prevent a mat of solid substance from building up on the filter.

2. A method as recited in claim 1 wherein the sample liquid comprises a pulp and paper industry process liquid; and wherein (c) is practiced to provide less than 0.1% of the flow of sample liquid from (a) as the minor flow passed through the filter.

3. A method as recited in claim 2 further comprising using the filtered sample from (c) to determine the content of at least one of dissolved and colloidal substances therein.

4. A method as recited in claim 3 wherein (c) is further practiced by passing the liquid through the filter at a velocity of about 1 mm/sec.

5. A method as recited in claim 1 wherein (c) is practiced so as to not noticeably influence the consistency of the flow of sample liquid in (a).

6. A method as recited in claim 1 wherein (d) is practiced using an impeller rotating adjacent the filter.

7. A method as recited in claim 1 wherein the sample flow chamber comprises a substantially cylindrical flow chamber having an inlet at a first end, and an outlet at a second end opposite the first end, and wherein the filter is in a side wall of the cylindrical flow chamber so that liquid passing through the filter moves substantially perpendicularly to the direction of flow of liquid from the inlet to the outlet; and wherein (d) is practiced solely by passing the sample liquid at high velocity along the filter.

8. A method as recited in claim 1 wherein (c) is practiced by passing the liquid through a polymer membrane filter having a thickness of about 7–23 microns, a porosity of about 4–20%, and a pore size of between 0.1–12 microns.

9. A method as recited in claim 1 wherein (c) is further practiced by passing the liquid through the filter at a velocity of less than 10 mm/sec.

10. A method as recited in claim 1 wherein the sample liquid comprises a pulp and paper industry process liquid; further comprising using the filtered sample from (c) to determine the content of at least one of dissolved and colloidal substances therein.

11. A method as recited in claim 10 wherein (c) is further practiced by passing the liquid through the filter at a velocity of less than 10 mm/sec and by controlling the flow of liquid through the filter by controlling a valve on the opposite side of the filter from the filtrate flow chamber.

12. A method as recited in claim 1 wherein (a)–(c) are practiced at least in part by applying pressure to the liquid being sampled from upstream of the sample flow chamber, or by applying vacuum thereto downstream of the sample flow chamber.

13. A method as recited in claim 12 wherein (c) is further practiced by controlling the flow of liquid through the filter by controlling a valve on the opposite side of the filter from the filtrate flow chamber.

14. Apparatus for obtaining a filtered sample for the determination of at least one of dissolved and colloidal substances, comprising:

a sample flow chamber having a side wall and a bottom, and constructed so that a continuous flow of sample liquid may be provided therethrough;

a filtrate flow chamber;

a filter connecting said sample flow chamber with said filtrate flow chamber, said filter disposed in said side wall or bottom of said sample flow chamber; and means for causing a flow of the sample liquid from said sample flow chamber through said filter corresponding to less than 1% of the flow of sample liquid in said sample flow chamber, to produce a solid substance removed from the flow of sample liquid to provide a filtered sample in said filtrate chamber which is suitable for use for the determination of at least one of dissolved and colloidal substances therein.

15. Apparatus as recited in claim 14 wherein said means for causing a flow of the sample liquid through the filter corresponding to less than 1% of the flow of sample liquid in the sample flow chamber comprising a conduit leading away from the filtrate flow chamber, and a valve in the conduit.

16. Apparatus as recited in claim 14 wherein said means for causing a flow of the sample liquid through the filter corresponding to less than 1% of the flow of sample liquid in the sample flow chamber comprising a conduit leading away from the filtrate flow chamber, and a vacuum pump connected to said conduit.

17. Apparatus as recited in claim 14 wherein said means for causing a flow of the sample liquid through the filter causes a flow of the sample liquid through the filter corresponding to less than 0.1% of the flow of sample liquid in the sample flow chamber.

18. Apparatus as recited in claim 14 further comprising means for preventing buildup of solid substances on said filter.

19. Apparatus as recited in claim 18 wherein said means for preventing buildup of solid substances on said filter comprises a rotating impeller adjacent said filter.

20. Apparatus as recited in claim 18 wherein said sample flow chamber comprises a substantially cylindrical flow chamber having an inlet at a first end, and an outlet at a second end opposite the first end; and wherein said filter is in said side wall of said cylindrical flow chamber so that liquid passing through the filter moves substantially perpendicularly to the direction of flow of liquid from the inlet to the outlet; and wherein said means for preventing buildup solely comprises positioning said filter adjacent the flow of liquid from said inlet to said outlet so that the sample liquid at high velocity along the filter.

21. Apparatus as recited in claim 14 wherein said filter comprises a nonwoven polymer membrane filter having a thickness of about 7–23 microns, a porosity of about 4–20%, and a pore size of 0.1–12 microns.

22. Apparatus as recited in claim 14 wherein said sample flow chamber, filter, and filtrate flow chamber comprise a first sample flow chamber, filter, and filtrate flow chamber, and further comprising at least a second sample flow chamber, second filter, and second filtrate flow chamber, disposed in parallel with said first sample flow chamber, filter, and filtrate flow chamber, said at least a second filter having a different pore size than said first filter.

23. Apparatus as recited in claim 14 further comprising a first suction pump for pulling the flow of sample liquid through said sample flow chamber, and a second suction pump for pulling filtrate through said filter.

* * * * *